(12) United States Patent
Traynor et al.

(10) Patent No.: US 8,911,461 B2
(45) Date of Patent: Dec. 16, 2014

(54) SUTURE CUTTER AND METHOD OF CUTTING SUTURE

(75) Inventors: Kate E. Traynor, Atkinson, NH (US); Steven D. Cahalane, Pelham, NH (US); Edward I. McNamara, Chelmsford, MA (US); Joseph A. Meranda, Lowell, MA (US); Paul T. Modoono, Chelmsford, MA (US); Joseph P. Lane, Methuen, MA (US); Aaron M. Call, Lowell, MA (US)

(73) Assignee: Mitralign, Inc., Tewksbury, MA (US)

( * ) Notice: Subject to any disclaimer, the term of this patent is extended or adjusted under 35 U.S.C. 154(b) by 1461 days.

(21) Appl. No.: 11/935,054

(22) Filed: Nov. 5, 2007

(65) Prior Publication Data

US 2008/0228198 A1    Sep. 18, 2008

Related U.S. Application Data

(63) Continuation-in-part of application No. 11/685,240, filed on Mar. 13, 2007, now abandoned.

(51) Int. Cl.
*A61B 17/32* (2006.01)
*A61B 17/04* (2006.01)

(52) U.S. Cl.
CPC .................................. *A61B 17/0467* (2013.01)
USPC ............ 606/170; 606/167; 606/139; 606/148

(58) Field of Classification Search
USPC ......... 606/138, 139, 147, 148, 167, 168, 170, 606/171, 232; 623/2.11, 2.36, 2.37; 600/567; 30/278
See application file for complete search history.

(56) References Cited

U.S. PATENT DOCUMENTS

| | | | |
|---|---|---|---|
| 2,143,910 A | 1/1939 | Didusch | |
| 3,328,876 A * | 7/1967 | Hoppe | 606/138 |
| 3,674,014 A | 7/1972 | Tillander | |
| 3,794,041 A | 2/1974 | Frei et al. | |
| 3,841,521 A | 10/1974 | Jarvik | |
| 3,959,960 A * | 6/1976 | Santos | 606/82 |
| 3,986,493 A | 10/1976 | Hendren, III | |

(Continued)

FOREIGN PATENT DOCUMENTS

| | | |
|---|---|---|
| EP | 1016377 A2 | 7/2000 |
| EP | 2181670 | 5/2010 |

(Continued)

OTHER PUBLICATIONS

Cardiac Surgery Renaissance, Anatomical Landscape; Composite Profile of CABG and Valve Procedures, Apr. 25, 1996, Cardiology Roundtable Interviews.

(Continued)

*Primary Examiner* — Mark Mashack
*Assistant Examiner* — Jing Ou
(74) *Attorney, Agent, or Firm* — Leason Ellis LLP (57) ABSTRACT

Suture cutters and methods of cutting suture in a surgical procedure. The suture cutter may include an actuator, an intermediate cannula portion and a movable cutting assembly. The cutting assembly may be operatively coupled to the actuator and include a cutting element. An adjustably sized cutting window receives the suture. The adjustably sized cutting window may be bound on at least one side with the cutting element for cutting the suture received inside the cutting window. Actuation moves the cutting assembly to cut the suture.

13 Claims, 9 Drawing Sheets

(56) References Cited

U.S. PATENT DOCUMENTS

| | | | |
|---|---|---|---|
| 3,995,619 A | * | 12/1976 | Glatzer .................. 600/550 |
| 4,042,979 A | | 8/1977 | Angell |
| 4,055,861 A | | 11/1977 | Carpentier et al. |
| 4,258,705 A | | 3/1981 | Sorensen et al. |
| 4,369,787 A | | 1/1983 | Lasner et al. |
| 4,489,446 A | | 12/1984 | Reed |
| 4,532,926 A | | 8/1985 | O'Holla |
| 4,809,713 A | | 3/1989 | Grayzel |
| 4,917,698 A | | 4/1990 | Carpentier et al. |
| 4,945,912 A | | 8/1990 | Langberg |
| 5,016,353 A | | 5/1991 | Iten |
| 5,041,129 A | | 8/1991 | Hayhurst et al. |
| 5,041,130 A | | 8/1991 | Cosgrove et al. |
| 5,061,277 A | | 10/1991 | Carpentier et al. |
| 5,104,407 A | | 4/1992 | Lam et al. |
| 5,123,914 A | | 6/1992 | Cope |
| 5,171,232 A | | 12/1992 | Castillo et al. |
| 5,171,259 A | | 12/1992 | Inoue |
| 5,192,302 A | | 3/1993 | Kensey et al. |
| 5,201,880 A | | 4/1993 | Wright et al. |
| 5,203,777 A | | 4/1993 | Lee |
| 5,304,190 A | * | 4/1994 | Reckelhoff et al. ........... 606/170 |
| 5,306,234 A | | 4/1994 | Johnson |
| 5,306,296 A | | 4/1994 | Wright et al. |
| 5,337,736 A | | 8/1994 | Reddy |
| 5,360,444 A | | 11/1994 | Kusuhara |
| 5,364,365 A | * | 11/1994 | Wortrich .................. 604/158 |
| 5,364,393 A | | 11/1994 | Auth et al. |
| 5,405,351 A | * | 4/1995 | Kinet et al. .................. 606/139 |
| 5,429,131 A | | 7/1995 | Scheinman et al. |
| 5,450,860 A | | 9/1995 | O'Connor |
| 5,452,513 A | * | 9/1995 | Zinnbauer et al. ............. 30/140 |
| 5,464,023 A | | 11/1995 | Viera |
| 5,527,332 A | * | 6/1996 | Clement .................. 606/171 |
| 5,545,178 A | | 8/1996 | Kensey et al. |
| 5,565,122 A | | 10/1996 | Zinnbauer et al. |
| 5,571,215 A | | 11/1996 | Sterman et al. |
| 5,593,424 A | | 1/1997 | Northrup |
| 5,607,471 A | | 3/1997 | Seguin et al. |
| 5,623,943 A | | 4/1997 | Hackett et al. |
| 5,626,590 A | | 5/1997 | Wilk |
| 5,640,955 A | | 6/1997 | Ockuly et al. |
| 5,669,919 A | | 9/1997 | Sanders et al. |
| 5,674,279 A | | 10/1997 | Wright et al. |
| 5,682,906 A | | 11/1997 | Sterman et al. |
| 5,690,656 A | | 11/1997 | Cope et al. |
| 5,706,827 A | | 1/1998 | Ehr et al. |
| 5,716,367 A | | 2/1998 | Koike et al. |
| 5,716,397 A | | 2/1998 | Myers |
| 5,716,399 A | | 2/1998 | Love |
| 5,776,080 A | | 7/1998 | Thome et al. |
| 5,776,189 A | | 7/1998 | Khalid |
| 5,797,939 A | | 8/1998 | Yoon |
| 5,813,996 A | | 9/1998 | St. Germain et al. |
| 5,824,066 A | | 10/1998 | Gross |
| 5,827,300 A | | 10/1998 | Fleega |
| 5,829,447 A | | 11/1998 | Stevens et al. |
| 5,830,224 A | | 11/1998 | Cohn et al. |
| 5,851,185 A | | 12/1998 | Berns |
| 5,860,920 A | | 1/1999 | McGee et al. |
| 5,868,733 A | | 2/1999 | Ockuly et al. |
| 5,879,366 A | | 3/1999 | Shaw |
| 5,888,240 A | | 3/1999 | Carpentier et al. |
| 5,906,579 A | | 5/1999 | Vander Salm et al. |
| 5,911,720 A | | 6/1999 | Bourne et al. |
| 5,928,224 A | | 7/1999 | Laufer |
| 5,931,818 A | | 8/1999 | Werp et al. |
| 5,944,738 A | | 8/1999 | Amplatz et al. |
| 5,967,984 A | | 10/1999 | Chu et al. |
| 5,980,515 A | | 11/1999 | Tu |
| 5,984,939 A | | 11/1999 | Yoon |
| 5,997,560 A | * | 12/1999 | Miller .................. 606/170 |
| 6,015,414 A | | 1/2000 | Werp et al. |
| 6,027,514 A | * | 2/2000 | Stine et al. .................. 606/159 |
| 6,042,581 A | | 3/2000 | Ryan et al. |
| 6,050,472 A | | 4/2000 | Shibata |
| 6,050,936 A | | 4/2000 | Schweich, Jr. et al. |
| 6,068,637 A | | 5/2000 | Popov et al. |
| 6,068,648 A | | 5/2000 | Cole et al. |
| 6,071,292 A | | 6/2000 | Makower et al. |
| 6,080,182 A | | 6/2000 | Shaw et al. |
| 6,099,460 A | | 8/2000 | Denker |
| 6,102,945 A | | 8/2000 | Campbell |
| 6,113,611 A | | 9/2000 | Allen et al. |
| 6,126,647 A | | 10/2000 | Posey et al. |
| RE36,974 E | | 11/2000 | Bonutti |
| 6,159,234 A | | 12/2000 | Bonutti et al. |
| 6,162,168 A | | 12/2000 | Schweich, Jr. et al. |
| 6,165,119 A | | 12/2000 | Schweich, Jr. et al. |
| 6,165,120 A | | 12/2000 | Schweich, Jr. et al. |
| 6,165,183 A | | 12/2000 | Kuehn et al. |
| 6,173,199 B1 | | 1/2001 | Gabriel |
| 6,190,353 B1 | | 2/2001 | Makower et al. |
| 6,197,017 B1 | | 3/2001 | Brock et al. |
| 6,206,895 B1 | | 3/2001 | Levinson |
| 6,210,432 B1 | | 4/2001 | Solem et al. |
| 6,231,587 B1 | | 5/2001 | Makower |
| 6,264,668 B1 | * | 7/2001 | Prywes .................. 606/167 |
| 6,267,781 B1 | | 7/2001 | Tu |
| 6,269,819 B1 | | 8/2001 | Oz et al. |
| 6,285,903 B1 | | 9/2001 | Rosenthal et al. |
| 6,287,317 B1 | | 9/2001 | Makower et al. |
| 6,298,257 B1 | | 10/2001 | Hall et al. |
| 6,306,133 B1 | | 10/2001 | Tu et al. |
| 6,312,447 B1 | | 11/2001 | Grimes |
| 6,319,263 B1 | | 11/2001 | Levinson |
| 6,332,089 B1 | | 12/2001 | Acker et al. |
| 6,332,893 B1 | | 12/2001 | Mortier et al. |
| 6,352,543 B1 | | 3/2002 | Cole |
| 6,385,472 B1 | | 5/2002 | Hall et al. |
| 6,401,720 B1 | | 6/2002 | Stevens et al. |
| 6,402,680 B2 | | 6/2002 | Mortier et al. |
| 6,402,781 B1 | | 6/2002 | Langberg et al. |
| 6,406,420 B1 | | 6/2002 | McCarthy et al. |
| 6,447,522 B2 | | 9/2002 | Gambale et al. |
| 6,461,366 B1 | | 10/2002 | Seguin |
| 6,500,184 B1 | | 12/2002 | Chan et al. |
| 6,524,303 B1 | | 2/2003 | Garibaldi |
| 6,530,952 B2 | | 3/2003 | Vesely |
| 6,537,198 B1 | | 3/2003 | Vidlund et al. |
| 6,537,314 B2 | | 3/2003 | Langberg et al. |
| 6,542,766 B2 | | 4/2003 | Hall et al. |
| 6,544,230 B1 | | 4/2003 | Flaherty et al. |
| 6,554,852 B1 | | 4/2003 | Oberlander |
| 6,562,019 B1 | | 5/2003 | Sell |
| 6,565,562 B1 | | 5/2003 | Shah et al. |
| 6,589,208 B2 | | 7/2003 | Ewers et al. |
| 6,594,517 B1 | | 7/2003 | Nevo |
| 6,596,014 B2 | | 7/2003 | Levinson et al. |
| 6,619,291 B2 | | 9/2003 | Hlavka et al. |
| 6,626,899 B2 | | 9/2003 | Houser et al. |
| 6,626,919 B1 | | 9/2003 | Swanstrom |
| 6,626,930 B1 | | 9/2003 | Allen et al. |
| 6,629,534 B1 | | 10/2003 | St. Goar et al. |
| 6,629,921 B1 | | 10/2003 | Schweich, Jr. et al. |
| 6,655,386 B1 | | 12/2003 | Makower et al. |
| 6,656,221 B2 | | 12/2003 | Taylor et al. |
| 6,669,687 B1 | | 12/2003 | Saadat |
| 6,669,707 B1 | | 12/2003 | Swanstrom et al. |
| 6,676,702 B2 | | 1/2004 | Mathis |
| 6,689,164 B1 | | 2/2004 | Sequin |
| 6,699,263 B2 | | 3/2004 | Cope |
| 6,702,825 B2 | | 3/2004 | Frazier et al. |
| 6,702,826 B2 | | 3/2004 | Liddicoat et al. |
| 6,718,985 B2 | | 4/2004 | Hlavka et al. |
| 6,723,038 B1 | | 4/2004 | Schroeder et al. |
| 6,730,112 B2 | | 5/2004 | Levinson |
| 6,733,509 B2 | | 5/2004 | Nobles et al. |
| 6,736,808 B1 | | 5/2004 | Motamedi et al. |
| 6,746,472 B2 | | 6/2004 | Frazier et al. |
| 6,764,500 B1 | | 7/2004 | Muijs Van De Moer et al. |
| 6,769,434 B2 | | 8/2004 | Liddicoat et al. |
| 6,793,618 B2 | | 9/2004 | Schweich, Jr. et al. |
| 6,866,673 B2 | | 3/2005 | Oren et al. |

(56) References Cited

U.S. PATENT DOCUMENTS

| | | | |
|---|---|---|---|
| 6,913,608 B2 | 7/2005 | Liddicoat et al. |
| 6,921,407 B2 | 7/2005 | Nguyen et al. |
| 6,923,823 B1 | 8/2005 | Bartlett et al. |
| 6,942,694 B2 | 9/2005 | Liddicoat et al. |
| 6,945,978 B1 | 9/2005 | Hyde |
| 6,949,122 B2 | 9/2005 | Adams et al. |
| 6,964,674 B1 | 11/2005 | Matsuura et al. |
| 6,964,683 B2 | 11/2005 | Kowalsky et al. |
| 6,976,995 B2 | 12/2005 | Mathis et al. |
| 7,004,958 B2 | 2/2006 | Adams et al. |
| 7,037,334 B1 | 5/2006 | Hlavka et al. |
| 7,101,395 B2 | 9/2006 | Tremulis et al. |
| 7,115,110 B2 | 10/2006 | Frazier et al. |
| 7,166,127 B2 | 1/2007 | Spence et al. |
| 7,211,094 B2 | 5/2007 | Gannoe et al. |
| 7,247,134 B2 | 7/2007 | Vidlund et al. |
| 7,731,732 B2 | 6/2010 | Ken |
| 7,749,250 B2 | 7/2010 | Stone et al. |
| 7,771,455 B2 | 8/2010 | Ken |
| 7,883,538 B2 | 2/2011 | To et al. |
| 7,931,580 B2 | 4/2011 | Gertner et al. |
| 8,172,871 B2 | 5/2012 | Ken |
| 2001/0005787 A1 | 6/2001 | Oz et al. |
| 2001/0039436 A1 | 11/2001 | Frazier et al. |
| 2001/0049492 A1 | 12/2001 | Frazier et al. |
| 2002/0013571 A1 | 1/2002 | Goldfarb et al. |
| 2002/0016628 A1 | 2/2002 | Langberg et al. |
| 2002/0019649 A1 | 2/2002 | Sikora et al. |
| 2002/0026198 A1 | 2/2002 | Ockuly et al. |
| 2002/0026216 A1 | 2/2002 | Grimes |
| 2002/0029080 A1 | 3/2002 | Mortier et al. |
| 2002/0042621 A1 | 4/2002 | Liddicoat et al. |
| 2002/0072758 A1 | 6/2002 | Reo et al. |
| 2002/0087169 A1 | 7/2002 | Brock et al. |
| 2002/0087173 A1 | 7/2002 | Alferness et al. |
| 2002/0087178 A1 | 7/2002 | Nobles et al. |
| 2002/0095167 A1 | 7/2002 | Liddicoat et al. |
| 2002/0100485 A1 | 8/2002 | Stevens et al. |
| 2002/0103532 A1 | 8/2002 | Langberg et al. |
| 2002/0107531 A1 | 8/2002 | Schreck et al. |
| 2002/0128708 A1 | 9/2002 | Northrup, III et al. |
| 2002/0156526 A1 | 10/2002 | Hlavka et al. |
| 2002/0165535 A1 | 11/2002 | Lesh et al. |
| 2002/0169359 A1 | 11/2002 | McCarthy et al. |
| 2002/0169502 A1 | 11/2002 | Mathis |
| 2002/0169504 A1 | 11/2002 | Alferness et al. |
| 2002/0173841 A1 | 11/2002 | Ortiz et al. |
| 2002/0183766 A1 | 12/2002 | Seguin |
| 2002/0183836 A1 | 12/2002 | Liddicoat et al. |
| 2002/0183837 A1 | 12/2002 | Streeter et al. |
| 2002/0183838 A1 | 12/2002 | Liddicoat et al. |
| 2002/0183841 A1 | 12/2002 | Cohn et al. |
| 2002/0188170 A1 | 12/2002 | Santamore et al. |
| 2003/0018358 A1 | 1/2003 | Saadat |
| 2003/0069593 A1 | 4/2003 | Tremulis et al. |
| 2003/0069636 A1 | 4/2003 | Solem et al. |
| 2003/0078465 A1 | 4/2003 | Pai et al. |
| 2003/0078654 A1 | 4/2003 | Taylor et al. |
| 2003/0078671 A1 | 4/2003 | Lesniak et al. |
| 2003/0083538 A1 | 5/2003 | Adams et al. |
| 2003/0105474 A1 | 6/2003 | Bonutti |
| 2003/0105520 A1 | 6/2003 | Alferness et al. |
| 2003/0120340 A1 | 6/2003 | Liska et al. |
| 2003/0130730 A1 | 7/2003 | Cohn et al. |
| 2003/0144697 A1 | 7/2003 | Mathis et al. |
| 2003/0160721 A1 | 8/2003 | Gilboa et al. |
| 2003/0171776 A1 | 9/2003 | Adams et al. |
| 2003/0171806 A1 | 9/2003 | Mathis et al. |
| 2003/0199974 A1 | 10/2003 | Lee et al. |
| 2003/0204205 A1* | 10/2003 | Sauer et al. ............ 606/232 |
| 2003/0208195 A1 | 11/2003 | Thompson et al. |
| 2003/0212453 A1 | 11/2003 | Mathis et al. |
| 2003/0220685 A1 | 11/2003 | Hlavka et al. |
| 2003/0233142 A1 | 12/2003 | Morales et al. |
| 2004/0003819 A1 | 1/2004 | St. Goar et al. |
| 2004/0019378 A1 | 1/2004 | Hlavka et al. |
| 2004/0024414 A1 | 2/2004 | Downing |
| 2004/0030382 A1 | 2/2004 | St. Goar et al. |
| 2004/0039442 A1 | 2/2004 | St. Goar et al. |
| 2004/0044364 A1 | 3/2004 | DeVries et al. |
| 2004/0049211 A1 | 3/2004 | Tremulis et al. |
| 2004/0092962 A1 | 5/2004 | Thornton et al. |
| 2004/0093023 A1 | 5/2004 | Allen et al. |
| 2004/0097865 A1* | 5/2004 | Anderson et al. ............ 604/22 |
| 2004/0122456 A1 | 6/2004 | Saadat et al. |
| 2004/0127983 A1 | 7/2004 | Mortier et al. |
| 2004/0133063 A1 | 7/2004 | McCarthy et al. |
| 2004/0147958 A1 | 7/2004 | Lam et al. |
| 2004/0152947 A1 | 8/2004 | Schroeder et al. |
| 2004/0162568 A1 | 8/2004 | Saadat et al. |
| 2004/0167539 A1 | 8/2004 | Kuehn et al. |
| 2004/0167620 A1 | 8/2004 | Ortiz et al. |
| 2004/0172046 A1 | 9/2004 | Hlavka et al. |
| 2004/0186486 A1 | 9/2004 | Roue et al. |
| 2004/0186566 A1 | 9/2004 | Hindichs et al. |
| 2004/0193191 A1 | 9/2004 | Starksen et al. |
| 2004/0220473 A1 | 11/2004 | Lualdi |
| 2004/0236419 A1 | 11/2004 | Milo |
| 2004/0243153 A1 | 12/2004 | Liddicoat et al. |
| 2004/0243227 A1 | 12/2004 | Starksen et al. |
| 2004/0254598 A1* | 12/2004 | Schumacher et al. ........ 606/170 |
| 2004/0260317 A1 | 12/2004 | Bloom et al. |
| 2004/0260323 A1* | 12/2004 | Truwit et al. .............. 606/170 |
| 2005/0033446 A1 | 2/2005 | Deem et al. |
| 2005/0049634 A1 | 3/2005 | Chopra |
| 2005/0049681 A1 | 3/2005 | Greenhalgh et al. |
| 2005/0055087 A1 | 3/2005 | Starksen |
| 2005/0055089 A1 | 3/2005 | Macoviak et al. |
| 2005/0065550 A1 | 3/2005 | Starksen et al. |
| 2005/0065601 A1 | 3/2005 | Lee et al. |
| 2005/0075723 A1 | 4/2005 | Schroeder et al. |
| 2005/0107810 A1 | 5/2005 | Morales et al. |
| 2005/0107812 A1 | 5/2005 | Starksen et al. |
| 2005/0107871 A1 | 5/2005 | Realyvasquez et al. |
| 2005/0119523 A1 | 6/2005 | Starksen et al. |
| 2005/0119734 A1 | 6/2005 | Spence et al. |
| 2005/0119735 A1 | 6/2005 | Spence et al. |
| 2005/0125011 A1 | 6/2005 | Spence et al. |
| 2005/0131438 A1 | 6/2005 | Cohn |
| 2005/0143811 A1 | 6/2005 | Realyvasquez |
| 2005/0148815 A1 | 7/2005 | Mortier et al. |
| 2005/0149014 A1 | 7/2005 | Hauck et al. |
| 2005/0159810 A1 | 7/2005 | Filsoufi |
| 2005/0177228 A1 | 8/2005 | Solem et al. |
| 2005/0184122 A1 | 8/2005 | Hlavka et al. |
| 2005/0197693 A1 | 9/2005 | Pai et al. |
| 2005/0216039 A1 | 9/2005 | Lederman |
| 2005/0234481 A1* | 10/2005 | Waller ..................... 606/148 |
| 2005/0251157 A1 | 11/2005 | Saadat et al. |
| 2005/0251159 A1 | 11/2005 | Ewers et al. |
| 2005/0251202 A1 | 11/2005 | Ewers et al. |
| 2005/0251205 A1 | 11/2005 | Ewers et al. |
| 2005/0251206 A1 | 11/2005 | Maahs et al. |
| 2005/0251207 A1 | 11/2005 | Flores et al. |
| 2005/0251208 A1 | 11/2005 | Elmer et al. |
| 2005/0251209 A1 | 11/2005 | Saadat et al. |
| 2005/0251210 A1 | 11/2005 | Westra et al. |
| 2005/0267533 A1 | 12/2005 | Gertner |
| 2005/0267571 A1 | 12/2005 | Spence et al. |
| 2005/0283192 A1 | 12/2005 | Torrie et al. |
| 2005/0288694 A1 | 12/2005 | Solomon |
| 2006/0004410 A1* | 1/2006 | Nobis et al. ............... 606/232 |
| 2006/0009784 A1 | 1/2006 | Behl et al. |
| 2006/0069429 A1 | 3/2006 | Spence et al. |
| 2006/0142756 A1 | 6/2006 | Davies et al. |
| 2006/0161040 A1 | 7/2006 | McCarthy et al. |
| 2006/0178682 A1* | 8/2006 | Boehlke .................. 606/148 |
| 2006/0212045 A1 | 9/2006 | Schilling et al. |
| 2007/0005081 A1* | 1/2007 | Findlay et al. .............. 606/148 |
| 2007/0010857 A1 | 1/2007 | Sugimoto et al. |
| 2007/0055303 A1 | 3/2007 | Vidlund et al. |
| 2007/0080188 A1 | 4/2007 | Spence et al. |
| 2007/0106310 A1* | 5/2007 | Goldin et al. .............. 606/148 |
| 2007/0112424 A1 | 5/2007 | Spence et al. |

(56) References Cited

U.S. PATENT DOCUMENTS

| | | | |
|---|---|---|---|
| 2008/0228165 | A1 | 9/2008 | Spence et al. |
| 2008/0228265 | A1 | 9/2008 | Spence et al. |
| 2008/0228266 | A1 | 9/2008 | McNamara et al. |
| 2008/0228267 | A1 | 9/2008 | Spence et al. |
| 2008/0275503 | A1 | 11/2008 | Spence et al. |
| 2009/0018655 | A1 | 1/2009 | Brunelle et al. |

FOREIGN PATENT DOCUMENTS

| | | | |
|---|---|---|---|
| WO | 9604852 | A1 | 2/1996 |
| WO | 9900059 | A1 | 1/1999 |
| WO | 0003759 | A2 | 1/2000 |
| WO | 0044311 | A2 | 8/2000 |
| WO | 0060995 | A2 | 10/2000 |
| WO | 0067640 | A2 | 11/2000 |
| WO | 0200099 | A2 | 1/2002 |
| WO | 02051329 | A1 | 7/2002 |
| WO | 02096275 | A2 | 12/2002 |
| WO | 03001893 | A2 | 1/2003 |
| WO | 03007796 | A2 | 1/2003 |
| WO | 03053289 | A1 | 7/2003 |
| WO | WO 2004/037317 | | 5/2004 |
| WO | 2004045378 | A2 | 6/2004 |
| WO | 2004112658 | A1 | 12/2004 |
| WO | 2005011463 | A2 | 2/2005 |
| WO | 2005013832 | A1 | 2/2005 |
| WO | 2005025644 | A2 | 3/2005 |
| WO | WO 2005058239 | | 6/2005 |
| WO | 2006064490 | A1 | 6/2006 |
| WO | WO 2006105008 | | 10/2006 |
| WO | 2007005394 | A1 | 1/2007 |
| WO | WO 2008091391 | | 7/2008 |

OTHER PUBLICATIONS

F. Maisano et al., The Double-Orifice Technique as a Standardized Approach to Treat Mitral Regurgitation Due to Severe Myxomatous Disease: Surgical Technique, European Journal of Cardio-thoracis Surgery, 1998.

Douglas P. Zipes, MD et al., Ablation of Free Wall Accessory Pathways, Catheter Ablation of Arrhythmias, Chapter 8, 7 pgs., 1994.

Gsolt L. Nagy et al., Mitral Annuloplasty with a Suture Technique, European Journal of Cardio-thoracic Surgery 18, Aug. 15, 2000, 1 pg.

David L.S. Morales et al., Development of an Off Bypass Mitral Valve Repair, Department of Surgery, Columbia University, College of Physicians and Surgeons, New York, NY.

http://www.hsforum.com/vol2/issue2/1999-4963 tables.html.

http:/www.hsforum.com/vol2/issue2/1999-4963figures.html.

http://medtronic.com/cardiac/heartvalves/duran_band/.

European Patent Office, Supplementary Search Report in EP Application No. 02764186.9, Jan. 26, 2007.

European Patent Office, Supplementary Search Report in EP Application No. 02733960.5, Jan. 25, 2007.

European Patent Office, International Search Report and Written Opinion in PCT Application Serial No. PCT/US2006/024897, Dec. 6, 2006.

U.S. Patent and Trademark Office, Office Action in U.S. Appl. No. 10/948,922, Sep. 11, 2007.

U.S. Patent and Trademark Office, Office Action in U.S. Appl. No. 11/111,044, Jul. 16, 2007.

U.S. Patent and Trademark Office, Office Action in U.S. Appl. No. 10/622,207, May 21, 2007.

U.S. Patent and Trademark Office, Office Action in U.S. Appl. No. 10/622,207, Jul. 14, 2006.

U.S. Patent and Trademark Office, Office Action in U.S. Appl. No. 10/622,207, Aug. 23, 2005.

U.S. Patent and Trademark Office, Office Action in U.S. Appl. No. 10/622,207, Dec. 28, 2004.

European Patent Office, European Examination Report in Application Serial No. 02764186.9, Feb. 11, 2008.

U.S. Patent and Trademark Office, Office Action in U.S. Appl. No. 11/111,044, Feb. 26, 2008.

U.S. Patent and Trademark Office, International Search Report and Written Opinion in PCT Application No. PCT/US2008/056620, Oct. 15, 2008.

U.S. Patent and Trademark Office, International Search Report and Written Opinion in PCT Application No. PCT/US2008/080735, Dec. 17, 2008.

U.S. Patent and Trademark Office, Office Action in U.S. Appl. No. 10/949,133, Dec. 10, 2008.

U.S. Patent and Trademark Office, Office Action in U.S. Appl. No. 10/949,412, Aug. 6, 2008.

U.S. Patent and Trademark Office, Office Action in U.S. Appl. No. 10/689,872, Aug. 8, 2008.

U.S. Patent and Trademark Office, Office Action in U.S. Appl. No. 10/622,207, Apr. 11, 2008.

U.S. Patent and Trademark Office, Office Action in U.S. Appl. No. 10/948,923, Mar. 18, 2008.

* cited by examiner

SUTURE CUTTER AND METHOD OF CUTTING SUTURE

This application is a continuation-in-part of U.S. Ser. No. 11/685,240, filed on Mar. 13, 2007 (pending) and assigned to the assignee of the present invention. The disclosure of U.S. Ser. No. 11/685,240 is hereby fully incorporated by reference herein.

TECHNICAL FIELD

The invention generally relates to devices used to cut suture during surgery. In particular, the invention relates to devices for cutting suture during minimally invasive surgery, such as catheter-based surgical procedures.

BACKGROUND

Heart disease is the leading cause of death in the United States. Almost 2,000 Americans die of heart disease every day. There are many different types of pathologies that affect the heart. One of the most common pathologies is mitral valve insufficiency. Mitral valve insufficiency occurs when the mitral valve is unable to completely close off fluid communication between the left atrium and the left ventricle during systole. In this situation, the mitral valve leaflets fail to completely coapt or come together to thereby prevent oxygenated blood from flowing in a retrograde fashion from the left ventricle back into the left atrium.

The most common method for repairing mitral valve insufficiency today is open-heart surgery. During open heart surgery, the chest of the patient is opened to create a large enough cavity for access to the heart. One common surgical procedure involves sewing an annuloplasty ring onto the mitral valve annulus from above via an incision into the left atrium of the heart. Various other procedures exist involving the use of suture material in and around the heart.

Minimally invasive surgery, and especially transluminal or percutaneous delivery of instruments into a patient, has become more and more common in various surgical applications. A promising new area of heart surgery involves catheter-based minimally invasive surgery. Catheter-based minimally invasive surgery for mitral valve repair, for example, should lessen the risks that are normally associated with open-heart surgery and will lessen trauma to the patient associated with opening the chest and cutting into the wall of the heart.

One of the problems with using minimally invasive surgery in general, and even more specifically in connection with the heart, is that traditional suture cutting devices are not suitable. For example, conventional hand held scissors-type suture cutters are not suitable for a catheter-based minimally invasive procedure. Accordingly, improved minimally invasive suture cutting devices and methods for cutting suture in a minimally invasive surgery are needed.

SUMMARY OF THE INVENTION

In one illustrative embodiment, a suture cutter for cutting suture within the body of a patient includes an actuator for manipulation by a medical professional, an intermediate cannula portion operatively coupled to the actuator for insertion into the patient, and a cutting assembly operatively coupled to the intermediate cannula portion and actuator. In each embodiment the cannula may or may not be more specifically a catheter configured and sized for insertion into the vascular system of the patient.

More particularly, the cutting assembly includes an adjustably sized cutting window and the cutting assembly cuts a suture received inside of the cutting window as the size of the cutting window is reduced upon actuation of the actuator.

The cutting element itself may comprise a blade having a sharpened cutting edge, such as a single or double beveled cutting edge, or the cutting element may comprise other types of elements such as an element that may or may not be sharpened but may be energized with radiofrequency (RF) energy for purposes of burning through the suture during the cutting operation. The suture may be cut against an element serving as an "anvil" or the cutting element may move past the suture into a suitable receiving space, such as a slot. A cutting element housing structure may be provided and further comprise a first aperture on one side of the cutting element and a second aperture on an opposite side of the cutting element. In this embodiment, the suture is adapted to pass from the first aperture to the second aperture through the cutting window.

The actuator may further comprise a biasing element configured to maintain the cutting assembly normally biased into a non-cutting safety position or, in other words, a non-actuated position. The actuator then moves the cutting assembly into a cutting position against the bias provided by the biasing element. The biasing element itself may, for example, comprise a coil spring. The actuator may further comprise a trigger movable, such as through rotation transverse to the direction that the trigger is pulled, from an inactive position in which the trigger may not be used to move the cutting assembly to cut the suture to an active position in which the trigger may be used to move the cutting assembly to cut the suture.

A method of cutting a suture located within a patient is also provided and includes positioning a suture cutter within the patient, with the suture cutter including a cutting element and a second element at least partially defining an adjustably sized cutting window. The suture is directed through the cutting window and the size of the cutting window is reduced by moving at least one of the cutting element or the second element towards the suture. The suture is then cut with the cutting element.

Various additional or alternative features will become apparent to those of ordinary skill in the art upon review of the following detailed description of the illustrative embodiments.

BRIEF DESCRIPTION OF THE DRAWINGS

The accompanying drawings, which are incorporated in and constitute a part of this specification, illustrate representative embodiments of the invention.

DETAILED DESCRIPTION OF THE ILLUSTRATIVE EMBODIMENTS

Figure 1:
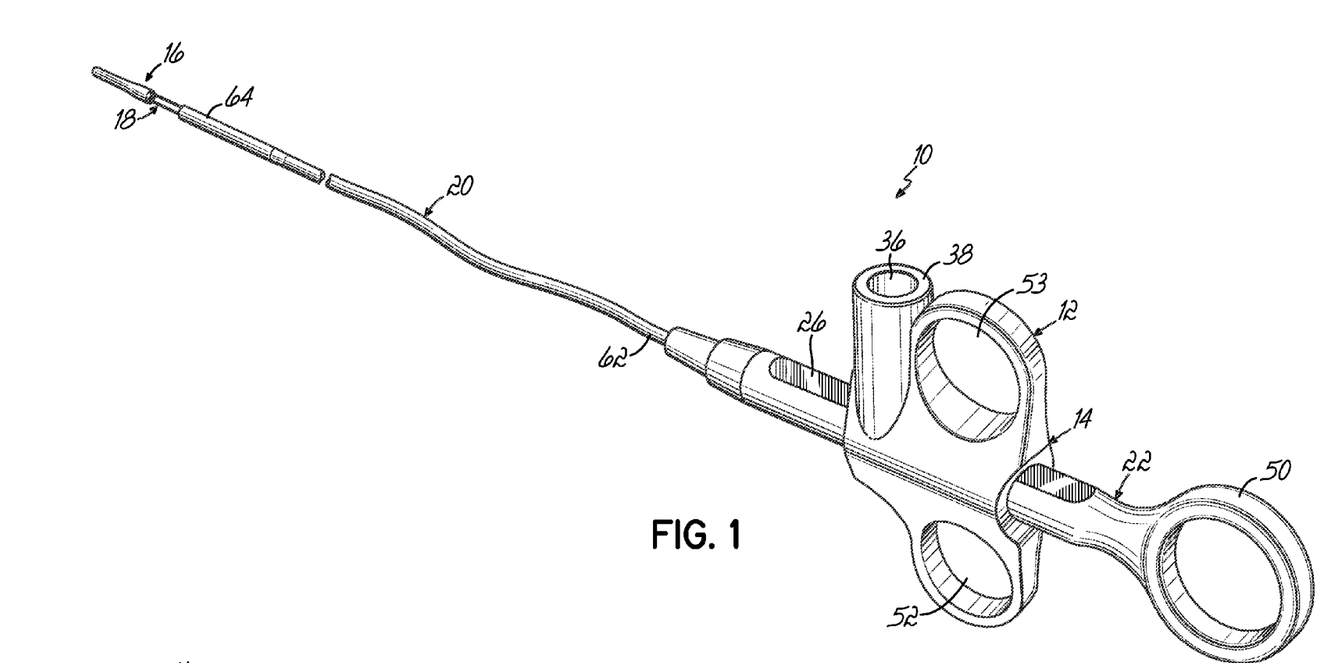
FIG. 1 is a perspective view of a suture cutter according to one illustrative embodiment.
Figure 2:
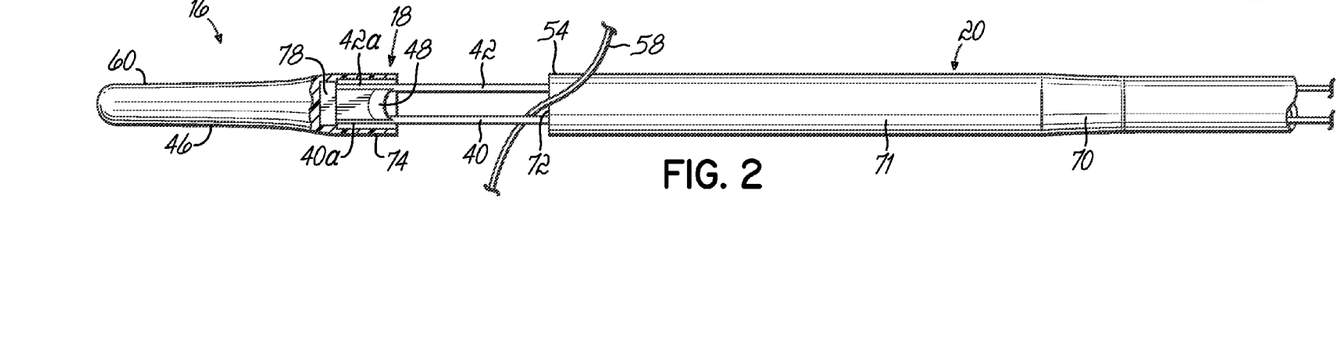
FIG. 2 is an enlarged perspective view of the axially movable distal tip of the suture cutter of FIG. 1.

FIGS. 1 and 2 illustrate a suture cutter 10 configured as a catheter device including a proximal portion 12 comprised of a handle assembly 14 and a distal portion 16 comprised of a cutting assembly 18. Suture cutter 10 may be used in any minimally invasive surgical procedure and directed into a patient's body with or without a guide cannula, such as a percutaneous catheter. Any other type of rigid or flexible guide cannula may also receive the suture cutter. A flexible intermediate catheter portion or other rigid or flexible cannula portion 20 extends between the proximal portion 12 and distal portion 16 of the suture cutter 10. The example given herein is a flexible cardiac catheter portion 20 sized and configured for introduction into the vascular system leading, for example, to the heart of a patient. However, it will be appreciated that other minimally invasive surgical techniques may be better practiced with a rigid cannula portion, such as certain endoscopic or laparoscopic techniques. As used herein, the term "catheter" is used to refer to the type of small diameter cannula that is inserted into a body lumen such as an artery in the vascular system. Although shown broken with a reduced length in FIG. 1, it will be appreciated that the overall length of the intermediate catheter portion 20 may be, for example, about 80 cm to about 140 cm as with other catheter devices to enable a doctor to direct the catheter device from a femoral artery of a patient into the heart of the patient. This would be useful, for example, when using the suture cutter 10 during a catheter based surgical procedure to repair the heart in some manner, such as during an annuloplasty or plication procedure on the mitral valve of the heart. For example, this type of repair procedure is described in more detail in U.S. patent application Ser. No. 11/174,951, the disclosure of which is hereby incorporated by reference herein, as well as the previously incorporated patent application, U.S. patent application Ser. No. 11/685,240.

Figure 3:
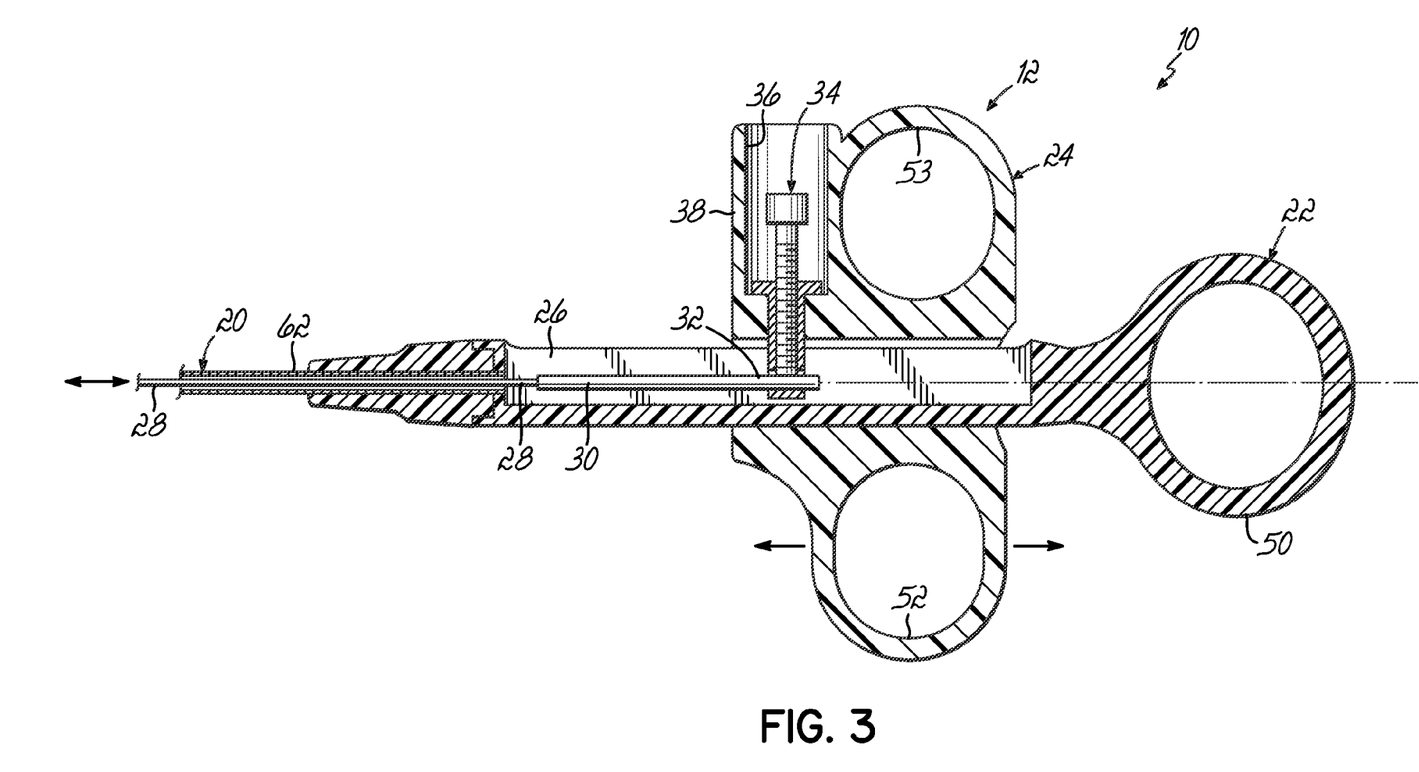
FIG. 3 is a cross sectional view of the suture cutter of FIG. 1 taken along the longitudinal axis at the actuator or proximal end of the suture cutter.

The handle assembly 14 includes a stationary grip portion 22 and a slidable or movable grip portion or trigger 24 mounted to the stationary grip portion 22 along a slot 26. FIG. 3 illustrates that the slidable grip portion 24 is rigidly coupled to a wire 28 enclosed in a tubular sheath 30 at the slot 26 and retained and slidable within the intermediate catheter portion 20. The proximal end 32 of the tubular sheath 30 is fixed to a threaded pin assembly 34 located within a cavity 36 in a cylindrical portion 38 of slidable grip portion 24. The pin 34, in one embodiment, can facilitate attachment of an energy source to provide energy to the wire 28, such as heat or RF (radio frequency) energy. The wire 28 divides into or is coupled to two separate wires 40, 42, as shown best in FIGS. 4A-4C, having distal ends 40a, 42a fixed to an axially movable distal cutting element or blade housing 46 that carries a blade 48 extending between the wires 40, 42.

Referring again to FIG. 1, the stationary grip portion 22 of the handle assembly 14 includes a ring 50 adapted to receive the thumb of the user, while the slidable grip 24 portion of the handle assembly 14 includes finger openings 52, 53. Thus, the handle assembly 14 operates somewhat analogously to a syringe except that actuation occurs by way of a proximally directed pulling action on the slidable grip portion 24. Referring again to FIGS. 1 and 2, when the slidable portion 24 of the handle assembly 14 moves distally the distal cutting element 46 moves away from a distal end 54 of the intermediate catheter portion 20 thereby exposing an area or window 56 between the two wires 40, 42. In the illustrated embodiment, the area is a window 56 defined between the two wires or other members 40, 42. The area could also be a window 56 that is only bound by one wire or other member in another embodiment or other types of windows apparent to those skilled in this art. Alternatively, when the movable or slidable grip portion 24 of the handle assembly 14 moves proximally along the slot 26, the wires 40, 42 are also drawn proximally thereby moving the distal cutting element 46 proximally towards one or more sutures 58 (only one suture being shown for illustration purposes).

The distal cutting element or blade housing 46 connects to the handle assembly 14 via the two wires 40, 42 in the illustrated embodiment, however, other embodiments could have only one wire or other type of connection member. The distal cutting element 46 includes the proximally facing blade 48 for cutting the suture 58 contained in the adjustably sized window 56 defined between the blade 48 and the intermediate catheter portion 20. In the illustrated embodiment, the blade 48 is concavely curved, but other embodiments could have a blade 48 with a different geometry. In the illustrated embodiment, the adjustably sized window 56 is bounded by the wires 40, 42, the distal end 54 of the intermediate catheter portion 20, and the sharpened edge of the blade 48. Those skilled in the art will recognize, for example, that the blade 48 may be distally positioned at the distal end 54 of the intermediate catheter portion 20 in other embodiments. The cutting element 46 includes a generally soft outer cover 60 made of a resilient material, such as foam or other soft polymeric or rubber material. The outer cover 60 helps to prevent damage to the heart tissue, for example, during introduction of the suture cutter into the heart and during cutting of the suture 58.

As further shown in FIG. 1, the intermediate catheter portion 20 has a proximal portion 62, a distal portion 64, and a lumen 66 (FIGS. 4A-4C) extending between the proximal and distal portions 62, 64. The intermediate catheter portion 20 generally comprises a tubular flexible sheath. In one embodiment, the tubular sheath could be formed of mesh material coated with a biocompatible material, such a surgical grade silicone or polymer. In an alternative embodiment, the tubular sheath could be formed of other materials as determined by those skilled in this art. The tubular sheath may be smooth and have a low coefficient of fluid friction to allow easy introduction through the patient's vascular system, for example, through a suitable guide catheter (not shown).

As better illustrated in FIG. 2, the intermediate catheter portion 20 includes a neck 70 that transitions a smaller diameter of the intermediate catheter portion 20 into a larger diameter ending at the cutting assembly 18. Significant portions of the wires 40, 42 are retained inside of the tubular sheath or intermediate catheter portion 20 for sliding movement inside of the lumen of the tubular sheath. The neck 70, however, indicates the transition from the hollow tubular sheath to a generally solid distal portion 71 shown in FIGS. 4A-4C. The generally solid distal portion 71 supports the wires 40, 42 as they move or slide during blade movement. The solid distal portion 71 also prevents significant amounts of body fluid from entering into the lumen 66. In addition, the solid distal portion 71 of the tubular sheath or intermediate catheter portion 20 provides a substantially flat cutting surface or anvil 72 (FIGS. 2 and 4A) on the distal end 54 for supporting a suture 58 during a cutting operation to be described below. The intermediate catheter portion 20 connects to the handle assembly 14 through a connector that tapers to a larger diameter before transitioning into the handle assembly 14. In the illustrated embodiment, the proximal portion 12 and the intermediate catheter portion 20 may be about 80 cm to about 140 cm in length. Those skilled in the art will recognize that a longer or shorter length may be used in different embodiments.

Figure 4A:
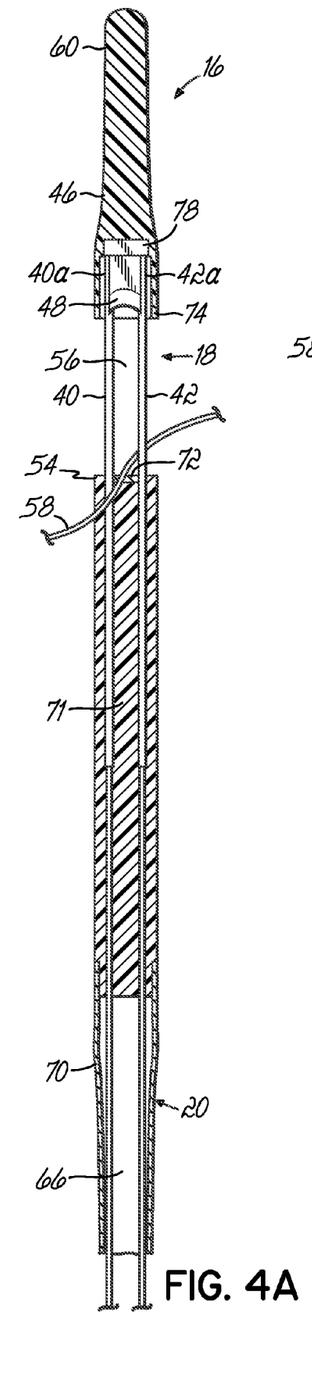
FIG. 4A is an enlarged cross-sectional elevational view of the axially movable distal tip of the suture cutter illustrated in FIG. 1 with a suture threaded through the cutting window.
Figure 4B:
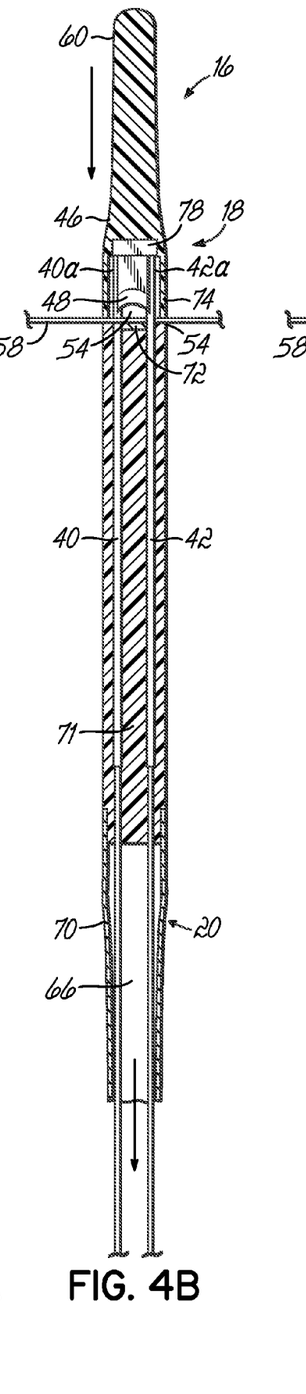
FIG. 4B is an enlarged cross-sectional elevational view of the axially movable distal tip of the suture cutter illustrated in FIG. 4A with the axially movable tip moving in a proximal direction prior to cutting the suture.
Figure 4C:
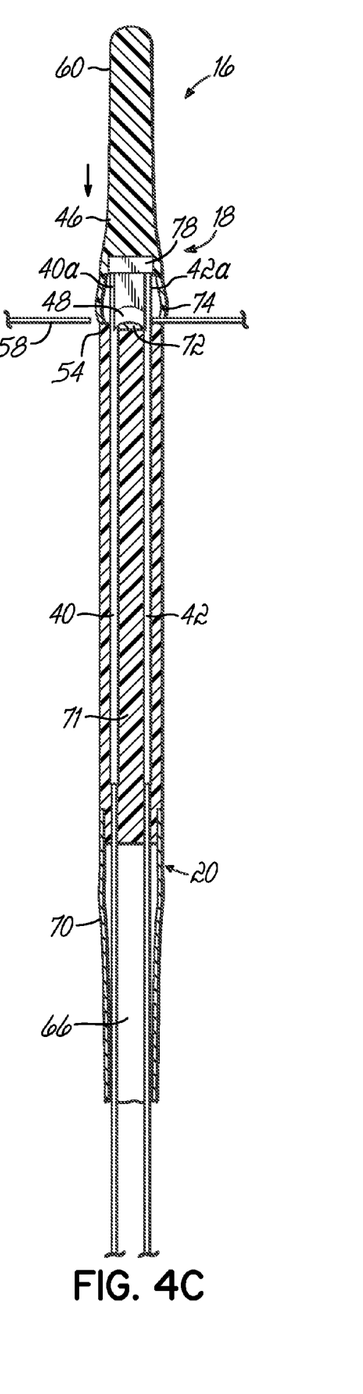
FIG. 4C is an enlarged cross-sectional elevational view of the axially movable distal tip of the suture cutter illustrated in FIG. 4B further illustrating the suture being cut.

FIGS. 4A-4C illustrate the cutting of a suture 58 in more detail. In FIG. 4A, the suture 58 is shown threaded through the window 56. The blade 48 is located inside a hood 74 defining an interior space inside of the cutting element 46. The blade 48 is rigidly fixed on a base 78 thereby holding the blade 48 in position during cutting. FIG. 4B illustrates that the proximal movement of the wires 40, 42 brings the cutting element 46 towards the distal end 54. The hood 74 contacts the suture 58 prior to contact by the blade 48 and therefore positions, holds or stabilizes the suture 58 for an efficient cutting action. FIG. 4C illustrates the blade 48 contacting and cutting the suture 58. The hood 74 is slightly compressed as the blade 48 cuts through the suture 58 and contacts the flat cutting surface or anvil 72 on the tubular sheath 68.

Figure 5:
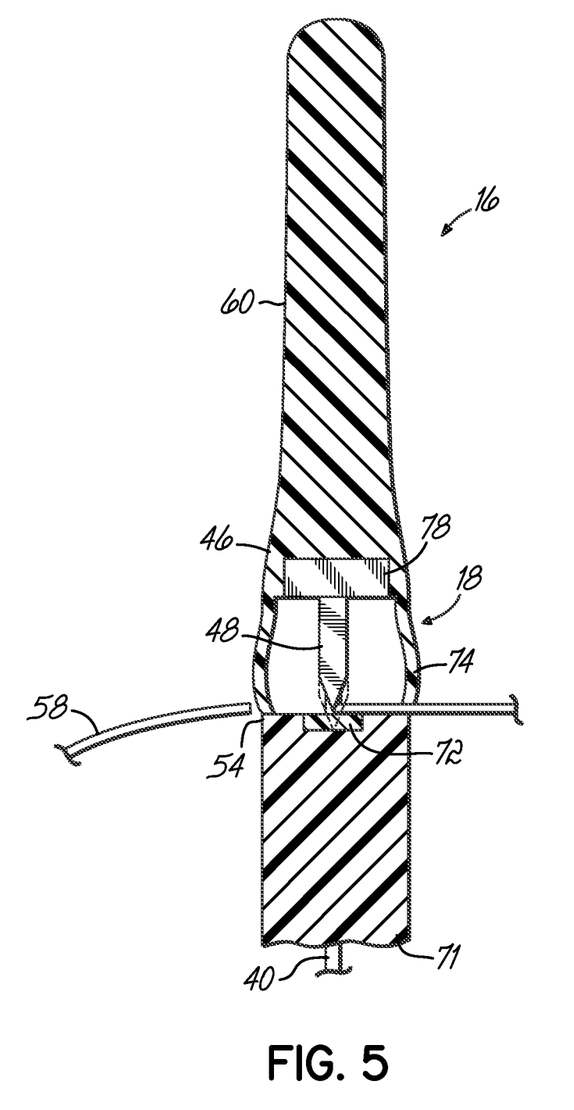
FIG. 5 is an enlarged cross-sectional view of the axially movable distal tip of the suture cutter illustrated in FIG. 1 illustrating the cooperation of the cutting blade with the anvil.

FIG. 5 provides additional detail about the structure of the blade 48 and the cutting element 46. FIG. 5 is rotated 1800 from the views of FIGS. 4A-4C. The geometry of the blade 48 facilitates enclosing the cutting surface or anvil 72 during the cutting of a suture 58. The flat surface or anvil 72 is formed of a resilient material, such as a resilient polymeric material, to allow the blade 48 to penetrate into and/or slightly compress the anvil 72.

Figure 6:
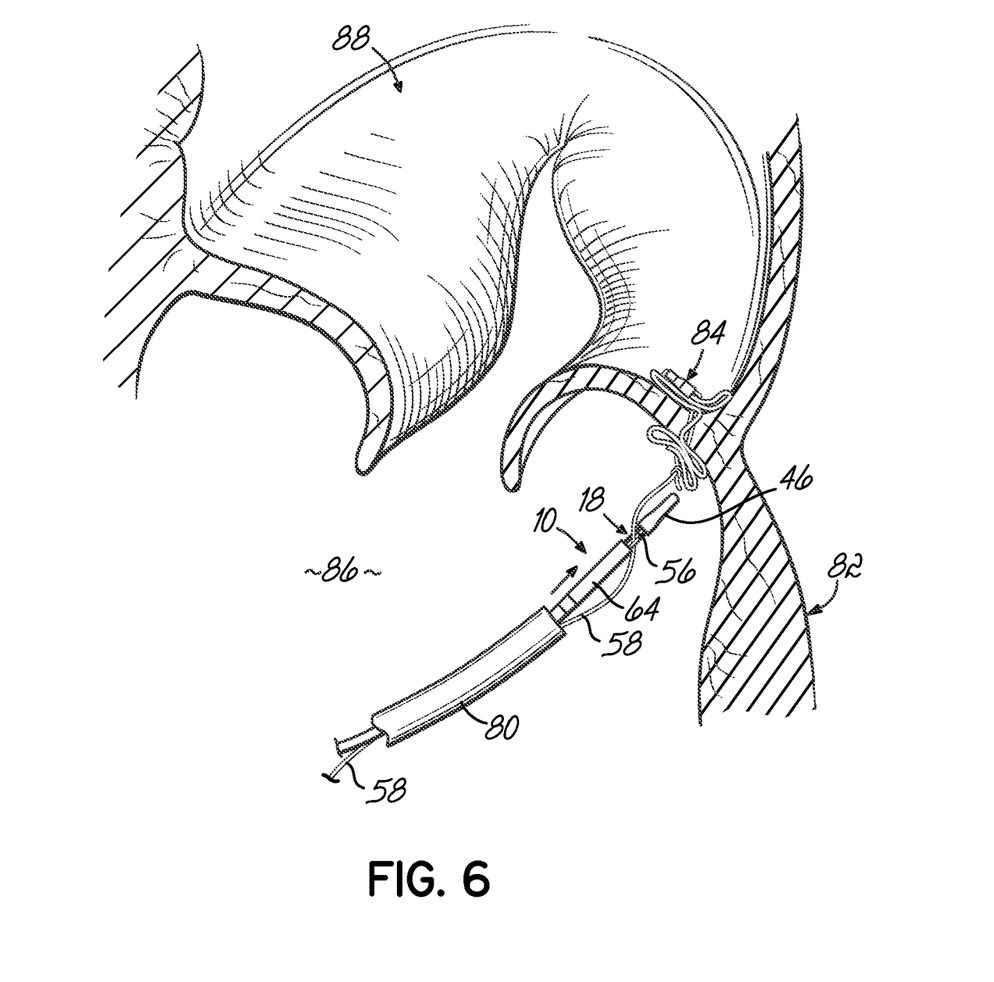
FIG. 6 is a perspective view illustrating the suture cutter of FIG. 1 inserted into a catheter and cutting a suture proximate to the mitral valve of the heart.

FIG. 6 illustrates one exemplary application of the suture cutter 10. Initially, a guide catheter 80 is snaked through the vascular system such that it may ultimately extend through the aorta, aortic valve and into the left ventricle 86 of the heart 82 of a patient in this illustrative example. A suture 58 extends from an anchor or fastener 84, or merely from the tissue, for example, and further extends into a guide catheter 80 exiting the patient at the proximal end (not shown) of the guide catheter 80. The suture 58 is threaded through the window 56 of the suture cutter 10, preferably although not necessarily prior to introduction of the suture cutter 10 into the patient. The suture cutter 10 is inserted into the guide catheter 80 and exits the guide catheter 80 inside the left ventricle 86 of the patient's heart 82 proximate to the mitral valve 88. The medical professional grips the suture cutter 10 at the handle assembly 14 (FIG. 1) by placing their middle finger and forefinger, respectively, into the finger openings 52, 53 and their thumb through the ring 50. The medical professional can manipulate the handle assembly 14 to position the cutting element 46 in the desired location. The medical professional then pulls back with their middle finger and forefinger and the slidable grip portion 24 moves proximally along the stationary grip portion 22. The proximal movement of the slidable grip portion 24 actuates the cutting element 46 and draws the blade 48 toward the cutting surface 72 and cuts the suture 58 as described in connection with FIGS. 4A-4C.

Figure 7:
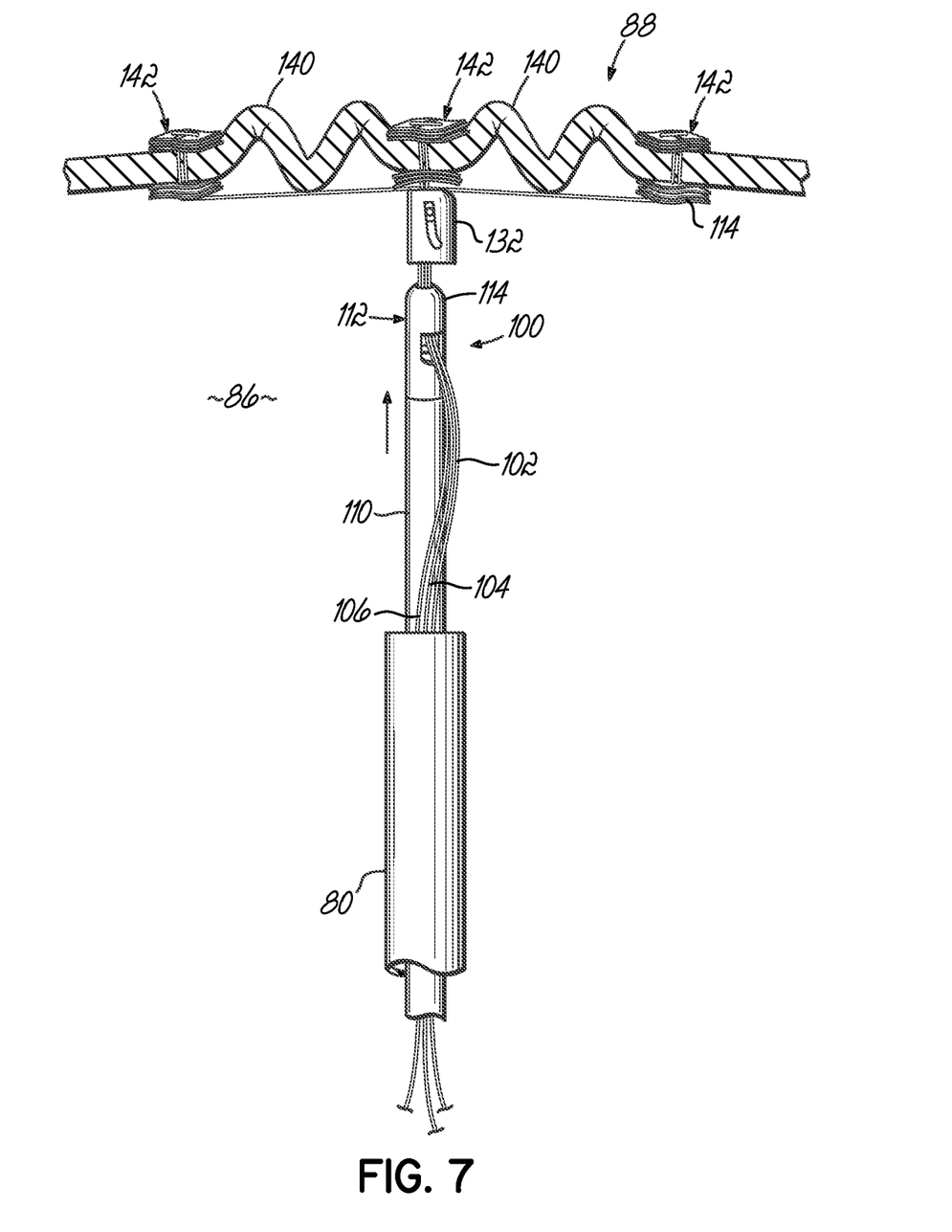
FIG. 7 is an elevational view showing the introduction of a suture cutter catheter in accordance with another embodiment and illustrated cutting multiple sutures or suture portions extending from a suture locker during a plication or annuloplasty procedure.
Figure 8A:
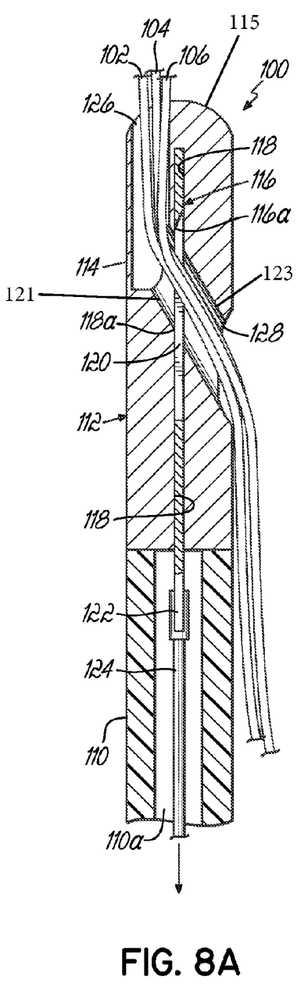
FIGS. 8A, 8B and 8C are cross sectional views of the distal end portion of the suture cutter showing the suture cutting operation.
Figure 8B:
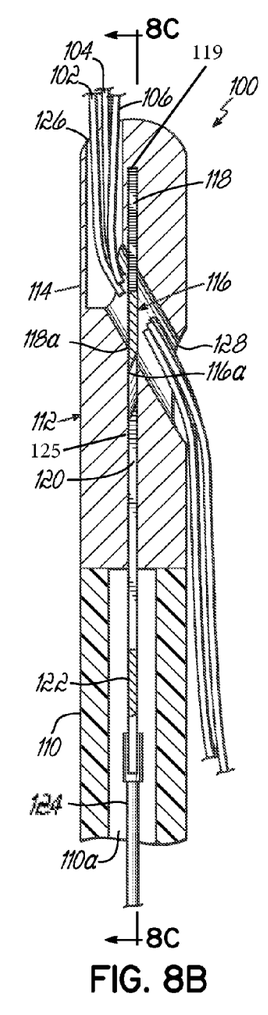
Figure 8C:
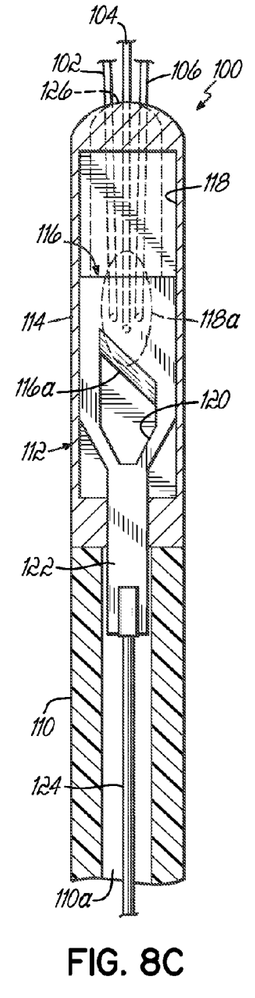

A suture cutter 100 in accordance with another embodiment is shown threaded along a plurality of sutures 102, 104, 106 through a guide catheter 108 as shown in FIG. 7. In this regard, the suture cutter 100 comprises an intermediate catheter portion 110 and a distal end portion comprising a cutting assembly 112. The cutting assembly 112 generally comprises a blade housing 114 and a reciprocating guillotine-style blade 116 slidably mounted therein with a cutting edge 116a as shown best in FIGS. 8A, 8B and 8C. The blade 116 is mounted for sliding, reciprocating movement within a slot 118 of blade housing 114. The slot 118 terminates in a closed end 119 that is located proximate a distal end 115 of the blade housing 114 and serves to limit a degree of travel of the cutting element (blade 116) disposed therein. As shown, the slot 118 is in the form of a longitudinal slot that has a planar construction that is complementary to and receives a planar blade 116. The blade 116 includes an opening 120 through which the sutures 102, 104, 106 extend to cross the path of the blade 116 within the housing 114. The opening 120 is thus in the form of a through hole that is integrally formed therein as shown in FIG. 8C. The blade 116 further includes a connecting end 122 coupled to an actuating element 124 which may, for example, comprise a wire or other member in a lumen 110a of catheter portion 110. The actuating element 124 may be pulled in the direction of the arrow in FIG. 8A to move the blade 116 in a proximal direction. The user may accomplish this with a suitable handle or trigger assembly coupled to actuator element 124, just as described in connection with the first embodiment, with the trigger mechanism (not shown) located outside the patient. It will be appreciated that any other type of actuator may be used instead of those shown and described. The blade housing 114 includes a first aperture 126 at its distal end 115 (distal tip) and a second aperture 128 along a lateral side thereof opposite to the first aperture 126. As shown in FIGS. 8A-8C, an internal channel or passageway (opening) is formed within the blade housing 114 (fixed in position) to connect the first aperture 126 to the second aperture 128 (the first and second apertures 126, 128 have a fixed location). Each of the first and second apertures 126, 128 are formed along an exterior surface of the blade housing. The internal channel has a first section that terminates at the first aperture 126 and a second section that terminates at the second aperture 128. As best shown in FIGS. 8A and 8B, the second section is an angled channel that extends across a width of the blade housing 114 and the first section is a longitudinally extending passageway that terminates in the first aperture 126. The angled channel is defined by an angled wall as a result of a bore being formed in and extending across a width of the blade housing 114, with the slot 118 (i.e., a bottom section 125 thereof) intersecting the angled channel so as to define a first wall section 121 that lies on one side of the slot 118 and the cutting element and a second wall section 123 that lies on the other side of the slot 118 and the cutting element. The first section is separated from the slot 118 by a wall as shown in FIGS. 8A and 8B. In this manner, the sutures 102, 104, 106 may extend into the blade housing 114 through aperture 126, through opening 120 of blade 116 and then through aperture 128 as shown in FIG. 8A. As further shown in FIGS. 8B and 8C, actuating element 124 may be pulled to move the blade 116 in a proximal direction such that the cutting edge 116a crosses edge 118a with or without a shearing action to cut the sutures 102, 104, 106 at points just proximal to a suture locker 132 as generally shown in FIG. 7 and used to secure one or more tissue plications 140 between tissue anchors 142. The cutting edge 116a may have any suitable design, including a double bevel configuration instead of the single bevel design shown. As shown in FIG. 8C, the cutting edge 116a is located along a distalmost side of the blade opening 120 resulting in the blade opening 120 (through hole formed in the blade) being proximal to the cutting edge 116a. The cutting edge 116a is thus formed at and is exposed along one side of the opening 120.

Figures 11, 12, 13:
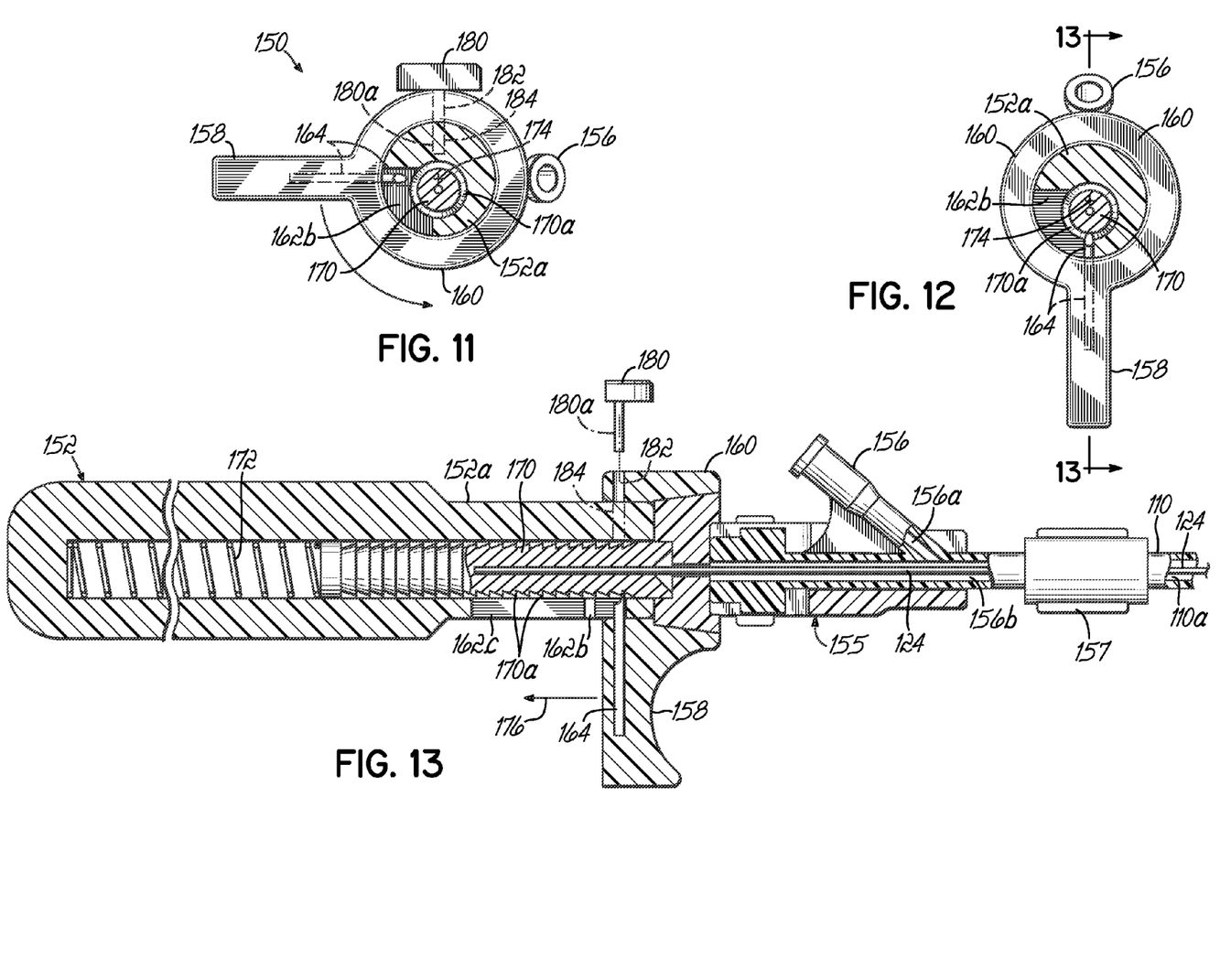
FIG. 11 is a cross sectional view taken along line 11-11 of FIG. 9 and showing the trigger mechanism in an inactive position.
FIG. 12 is a cross sectional view similar to FIG. 11, but illustrating the trigger mechanism in an active position.
FIG. 13 is a cross sectional view of the handle and actuating portion taken along line 13-13 of FIG. 12.

FIGS. 9-13 illustrate another embodiment of a suture cutter 150 threaded along a plurality of sutures 102, 104, 106. In this embodiment, like reference numerals used in previously discussed figures refer to like elements of structure with like function. The suture cutter 150 is illustrated as including an intermediate catheter portion 110 and a distal end portion comprising a cutting assembly 112 and a blade housing 114. The cutting assembly 112 and the intermediate catheter portion 110 may be configured and designed as previously shown and described and, therefore, no further description of these components is necessary. A proximal end of the suture cutter 150 includes a handle 152 and trigger mechanism 154. As shown best in FIG. 9, a connector 155 is affixed to the distal handle portion 152a. A fluid flushing port 156 is part of the connector 155 and connects with the intermediate catheter portion 110 by way of a connector 157 to allow the intermediate catheter portion 110 to be flushed with, for example, saline solution to eliminate any air in the intermediate catheter portion 110 just prior to use in a patient. For this purpose, a lumen 156a of portion 156 communicates with a lumen 156b, as shown in FIG. 13.

Figures 9, 10:
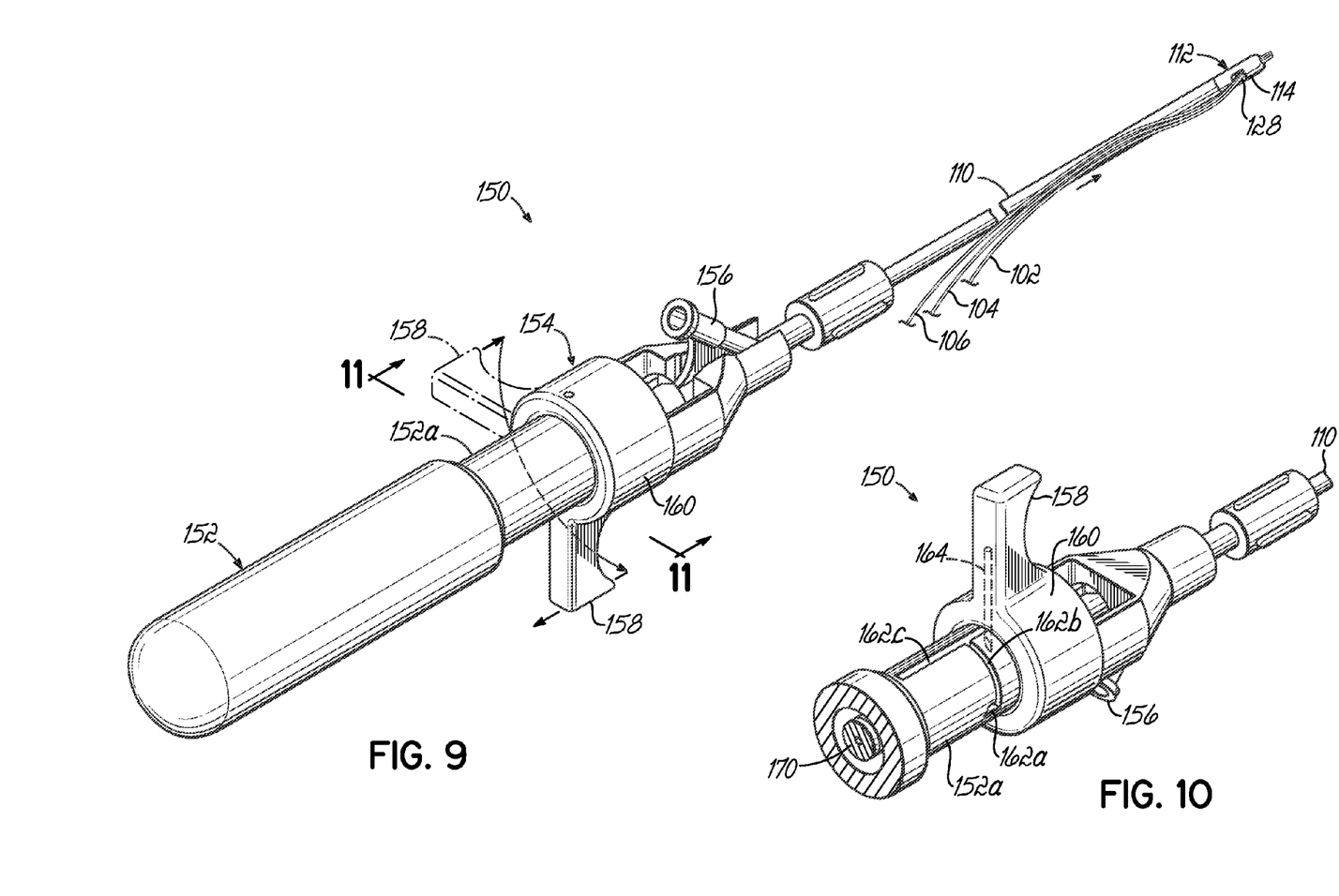
FIG. 9 is a perspective view of a suture cutter catheter in accordance with another embodiment and illustrated cutting multiple sutures or suture portions.
FIG. 10 is an enlarged view of an actuating portion of the suture cutter catheter shown in FIG. 9.

The trigger mechanism 154 is designed with a rotatable and longitudinally slidable trigger 158. The trigger mechanism 154 is designed to allow the suture cutter 150 to be "locked" and "unlocked." In the locked position, the trigger 158 may not be used to actuate the cutting assembly 112 to cut a suture, while in the unlocked position, the trigger 158 may be pulled to thereby actuate the cutting assembly 112 generally in the same manner as discussed above in connection with FIGS. 8A-8C. As shown best in FIG. 10, the trigger 158 includes an annular portion 160 slidably retained on a distal portion 152a of the handle 152. This distal portion 152a of the handle 152 includes grooves 162a, 162b, 162c that retain the end of a pin 164 fixed to the trigger 158. When the pin 164 is in a first short groove 162a contained in the distal handle portion 152a, the trigger 158 may not be pulled in a proximal direction and may not be used to actuate the blade associated with the cutting assembly 112 (FIG. 9). However, when the trigger 158 is rotated approximately 90° such that the pin 164 rotates through the transverse groove 162b and registers with the longer longitudinal groove 162c, the trigger 158 may then be pulled proximally. The inactive or locked trigger position is shown in FIG. 11, while the active or unlocked trigger position is shown in FIG. 12.

An actuating element 170 is located within the handle 152 and is spring-biased in a distal direction by a coil spring 172 to normally maintain the blade 116 in a non-cutting position (FIG. 8A). The actuating element 170 is located in an eccentric position relative to the axis of rotation 174 of the trigger 158 and annular section as best shown in FIGS. 11 and 12. Therefore, when the trigger 158 is rotated approximately 90°, the tip of the pin 164 will rotate from the position shown in FIG. 11 disengaged from the actuating element 170 to the position shown in FIG. 12 engaged with outer teeth or ridges 170a formed on the actuating element 170. Thus, as best shown in FIG. 13, once this registration occurs between the tip of the pin 164 and one of the teeth or ridges 170a, the trigger 158 may be pulled in a proximal direction as illustrated by the arrow 176. This moves the actuating element 170 including the attached wire portion 124 for purposes as previously described.

FIG. 13 also illustrates a removable locking element 180 that may be used to lock the actuating element 170 in place during storage and shipment of suture cutter 150. In this regard, the locking element 180 may be inserted through respective holes 182, 184 in the annular portion 160 and distal handle portion 152a such that a pin portion 180a prevents rotation of the trigger 158 and annular portion 160 from the locked or inactive position shown in FIG. 11 to the position shown in FIG. 12. The pin 180 may be removed by the user to allow rotation and then actuation of the trigger mechanism 154 as just described.

While the present invention has been illustrated by a description of various preferred embodiments and while these embodiments have been described in some detail, it is not the intention of the Applicant to restrict or in any way limit the scope of the appended claims to such detail. Additional advantages and modifications will readily appear to those skilled in the art. The various features of the invention may be used alone or in any combination depending on the needs and preferences of the user. This has been a description of the present invention, along with the preferred methods of practicing the present invention as currently known. However, the invention itself should only be defined by the appended claims.

What is claimed is:

1. A suture cutter for cutting a suture located within a patient, comprising:

an actuator for manipulation by a medical professional;

an intermediate cannula portion operatively coupled to the actuator; and a cutting assembly operatively coupled to the intermediate cannula portion and the actuator, the cutting assembly including a blade housing defined by a distal end, wherein the cutting assembly includes a movable cutting element that moves within a slot formed in the blade housing and includes an opening in the form of a through hole formed therein, and an adjustably sized cutting window that is at least partially defined by the opening, wherein the slot terminates in a closed end located proximate the distal end of the blade housing and is located between the cutting window and the distal end of the blade housing, the closed end of the slot limiting a degree of travel of the cutting element disposed therein, the blade housing having a first fixed aperture for permitting the suture to pass external to the blade housing and a second fixed aperture for permitting the suture to pass external to the blade housing, each of the first and second apertures being formed and open along an exterior surface of the blade housing, the first aperture being longitudinally offset from the second aperture and closer to the distal end compared to the second aperture, wherein the blade housing has a fixed channel formed therein that connects and extends between the first aperture and the second aperture with the slot intersecting the channel, the fixed channel being defined by an angled wall as a result of a bore being formed in the blade housing, the slot intersecting the fixed channel such that a first section of the angled wall lies on one side of the slot and cutting element, while a second section of the angled wall lies on an opposite side of the slot and cutting element, wherein the cutting assembly is configured to cut a suture received inside of the cutting window as the size of the cutting window is reduced upon actuation of the actuator.

2. The suture cutter of claim 1, wherein the cutting element further comprises a blade having a sharpened cutting edge.

3. The suture cutter of claim 2, wherein the blade is located along a distalmost side of the opening resulting in the through hole being formed proximal to the blade.

4. The suture cutter of claim 1, wherein the cutting element is disposed on one side of the cutting window and at least a portion of the slot is disposed on an opposite side of the cutting window, wherein the cutting window is configured for receiving a suture that is cut as the cutting element moves into the slot.

5. The suture cutter of claim 4, wherein the slot comprises a longitudinal slot formed in the blade housing.

6. The suture cutter of claim 4, wherein the first aperture is located on one side of the cutting element and the second aperture is located on an opposite side of the cutting element, wherein the channel is configured for receiving a suture that passes from the first aperture to the second aperture through the cutting window.

7. The suture cutter of claim 1, wherein the intermediate cannula portion further comprises a catheter configured to be directed through the vascular system of the patient.

8. The suture cutter of claim 1, wherein the actuator further comprises a biasing element configured to maintain the cutting assembly normally biased into a non-cutting safety position.

9. The suture cutter of claim 8, wherein the actuator is configured to move the cutting assembly into a cutting position against the bias provided by the biasing element.

10. The suture cutter of claim 1, wherein the actuator further comprises a trigger movable from an inactive position in which the trigger cannot be used to actuate the cutting assembly to cut the suture to an active position in which the trigger can be used to actuate the cutting assembly to cut the suture.

11. The suture cutter of claim 1, wherein the channel comprises a longitudinal section which runs longitudinally and terminates in the first aperture and an angled section that is formed at an angle across a width of the blade housing and terminates in the second aperture.

12. The suture cutter of claim 11, wherein the longitudinal section is separated from the distal end of the slot by a wall.

13. The suture cutter of claim 11, wherein the first aperture is formed at the distal end of the blade housing.

\* \* \* \* \*